US008168755B2

(12) United States Patent
Cardone et al.

(10) Patent No.: US 8,168,755 B2
(45) Date of Patent: May 1, 2012

(54) ANTIBODIES SPECIFIC TO HETERODIMERS OF BCL-2 FAMILY AND USES THEREOF

(75) Inventors: Michael H. Cardone, Dorchester, MA (US); Anthony G. Letai, Medfield, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 57 days.

(21) Appl. No.: 12/437,127

(22) Filed: May 7, 2009

(65) Prior Publication Data

US 2009/0280510 A1    Nov. 12, 2009

Related U.S. Application Data

(60) Provisional application No. 61/051,206, filed on May 7, 2008.

(51) Int. Cl.
*C07K 16/00* (2006.01)
*C12P 21/08* (2006.01)
(52) U.S. Cl. ................ 530/387.1; 530/388.1; 530/389.1
(58) Field of Classification Search ........................ None
See application file for complete search history.

(56) References Cited

U.S. PATENT DOCUMENTS

2005/0191696 A1    9/2005    Goldmakher et al.
2006/0183687 A1    8/2006    Cory et al.
2008/0104721 A1    5/2008    Barsova et al.

OTHER PUBLICATIONS

Paul. Fundamental Immunology, 3rd Edition, 1993, pp. 292-295.*
Rudikoff, Giusti, Cook, and Scharff. Single amino acid substitution altering antigen-binding specificity. Proceedings of the National Academy of Sciences, 1982. vol. 79, pp. 1979-1983.*
Colman. Effects of amino acid sequence changes on antibody-antigen interactions. Research in Immunology, 1994. vol. 145, pp. 33-36.*
Mac Callum, Martin, and Thornton. Antibody-antigen interactions: contact analysis and binding site topography. Journal of Molecular Biology, 1996. vol. 262, pp. 732-745.*
Campbell. Monoclonal Antibody Technology, 1984, pp. 1-32.*
Letai et al., "Antiapoptotic BCL-2 is required for maintenance of a model leukemia," Cancer Cell, Sep. 2004, vol. 6, pp. 241-249.
Certo et al., "Mitochondria primed by death signals determine cellular addiction to antiapoptotic BCL-2 family members," Cancer Cell 9, May 2006, pp. 351-365.
Letai, "Diagnosing and exploiting cancer's addiction to blocks in apoptosis," Nature Reviews/Cancer, vol. 8, Feb. 2008, pp. 121-132.

* cited by examiner

*Primary Examiner* — Anne M. Gussow
(74) *Attorney, Agent, or Firm* — Cooley LLP

(57) ABSTRACT

Isolated antibodies specifically binding to heterodimers of the Bcl-2 family and uses thereof for detecting presence of Bcl-2 heterodimers in a patient.

3 Claims, 7 Drawing Sheets

A.

B.

C.

Binding agents, for example: Mab, IgG, Fab, scFv, aptamers

Multidomain Bcl-2 Family proteins

BH3 only protein

Heterodimer

Fluorescent labels

GamaBind Sepharose bead

A.

B.

C.

Anti VDAC labeled

Anti-Heterodimer Labeled

Multidomain Bcl-2 Family proteins

BH3 only protein

Heterodimer

VDAC

Mitochondria

A.

Detect primed mitochondria
Sample 1 (yellow bead)

Bead
5 micron

Detect primed mitochondria
Sample 2 (blue bead)

Detect primed mitochondria
Sample 3 (teal bead)

Detect unprimed mitochondria
Sample 4 (pink bead)

Mitochondria
1 micron

B.

Mitochondria primed with heterdimer-1, heterdimer-2, Or unprimed

Anti-VDAC

Anti-heterodimer-1 labeled with Fluor 1

Anti-heterodimer-2 labeled with Fluor 2

ANTIBODIES SPECIFIC TO HETERODIMERS OF BCL-2 FAMILY AND USES THEREOF

CROSS-REFERENCE TO RELATED APPLICATION

This application claims priority to U.S. Provisional Patent Application No. 61/051,206, filed May 7, 2008, the content of which is incorporated herein by reference in its entirety.

BACKGROUND OF THE INVENTION

Apoptosis is a process of programmed cell death mediated by a number of signaling pathways that converge at the mitochondria. A group of mitochondrial proteins, i.e., the Bcl-2 proteins, regulates this process. More specifically, pro-apoptotic and anti-apoptotic Bcl-2 proteins form heterodimers with their cognate regulating Bcl-2 proteins (i.e., the BH3-only Bcl-2 proteins), thereby executing cell death or survival signals.

Essentially all effective cancer drugs induce apoptosis in target cancer cells. However, different cancer cells respond to an apoptosis-inducing drug in different manners. This is due to the presence of different heterodimers between the pro/anti-apoptotic Bcl-2 proteins and the regulatory BH3-only Bcl-2 proteins in those cancer cells. Determining the presence of these heterodimers in a cancer patient helps assessing that patient's responsiveness to an apoptosis-inducing cancer drug.

SUMMARY OF THE INVENTION

One aspect of this invention features an isolated antibody that specifically binds to a heterodimer of the Bcl-2 family (i.e., a Bcl-2 heterodimer). The Bcl-2 family includes both Bcl-2 proteins (monomers) and naturally-occurring heterodimers formed between two Bcl-2 proteins. The heterodimer contains a first Bcl-2 protein (e.g., Bim, Bid, Bad, Puma, Noxa, Bak, Hrk, Bax, or Mule) and a second Bcl-2 protein (e.g., Mcl-1, Bcl-2, Bcl-XL, Bfl-1 or Bcl-w).

The antibody of this invention can be a monoclonal antibody, a polyclonal antibody, a chimeric antibody, or a humanized antibody. It also can be a functional fragment of a whole antibody, such as F(ab')$_2$, Fab', F(ab)$_2$, and Fab. Alternatively, the antibody of this invention is a single chain antibody, e.g., a single chain variable fragment (scFv).

Another aspect of this invention is a method for detecting the presence of a heterodimer of the Bcl-2 family using any of the antibodies described above. This method includes (i) providing a tissue sample suspected of having a heterodimer of the Bcl-2 family, (ii) contacting the sample with the antibody, (iii) detecting a signal indicative of binding of the antibody to the heterodimer, and (iv) determining the presence of the heterodimer in the sample based on the intensity of the signal. Examples of the heterodimer include Bim/Mcl-1 and Bim/Bcl-2. The tissue sample examined in this method can be a peripheral blood sample, a lymph-node sample, a bone marrow sample, or an organ tissue sample. Preferably, it is a mitochondrial fraction.

Also within the scope of this invention is a method for assessing whether a patient is sensitive or resistance to a drug that interferes with formation of a heterodimer of the Bcl-2 family based on the presence of that heterodimer in the patient. A cancer patient is sensitive to an apoptosis inducer that blocks formation of an anti-apoptotic Bcl-2 heterodimer if this heterodimer is present in that patient. A neurodegenerative disease or cardiovascular disease patient, on the other hand, is responsive to an apoptosis inhibitor that blocks formation of a pro-apoptotic Bcl-2 heterodimer if this heterodimer is present in that patient.

The details of one or more examples of the invention are set forth in the description below. Other features or advantages of the present invention will be apparent from the following drawings, detailed description of several examples, and also from the appended claims.

BRIEF DESCRIPTION OF THE DRAWINGS

The drawings are first described.

DETAILED DESCRIPTION OF THE INVENTION

Disclosed herein is an isolated antibody specific to a Bcl-2 heterodimer, i.e., a naturally-occurring heterodimer formed between two Bcl-2 proteins.

Bcl-2 proteins, found in mitochondria, are major regulators of the commitment to programmed cell death and executioners of death/survival signals. See Reed, Natural Clinical Practice Oncology, 3:388-398 (2006), Green et al., Cancer Cell 1:19-30 (2002), and Adams et al., Cold Spring Harb. Symp. Quant. Biol. 70:469-477 (2005). There are four sub-groups of Bcl-2 proteins: (i) multi-domain anti-apoptotic Bcl-2 proteins, (ii) multi-domain pro-apoptotic Bcl-2 proteins, (iii) activator BH3-only Bcl-2 proteins, and (iv) sensitizer BH3-only Bcl-2 proteins. Table 1 below lists major human Bcl-2 proteins and their GenBank accession numbers:

TABLE 1

| Human Bcl-2 Proteins | | |
|---|---|---|
| Bcl-2 Proteins | | GenBank Accession Numbers |
| Multi-domain Anti-Apoptotic | Bcl-2 | AAH27258 (Jul. 15, 2006) |
| | Bcl-XL | AAH19307 (Jul. 15, 2006) |

TABLE 1-continued

Human Bcl-2 Proteins

| Bcl-2 Proteins | | GenBank Accession Numbers |
|---|---|---|
| Bcl-2 Proteins | Mcl-1 | AAF64255 (Jul. 17, 2000) |
| | BCL-w | AAB09055 (Sep. 29, 1996) |
| | BFL-1 | Q16548 (Mar. 3, 2009) |
| Multi-domain | BAX | Q07812 (Apr. 14, 2009) |
| Pro-Apoptotic Bcl-2 Proteins | BAK | Q16611 (Apr. 14, 2009) |
| Sensitizer BH3-only Bcl-2 Proteins | BAD | CAG46757 (Jun. 29, 2004) |
| | BIK | CAG30276 (Oct. 16, 2008) |
| | NOXA | Q13794 (Mar. 3, 2009) |
| | HRK | AAC34931 (Sep. 9, 1998) |
| | BMF | AAH69328 (Aug. 19, 2004); AAH60783 (Jan. 27, 2004) |
| | PUMA | Q9BXH1 (Apr. 14, 2009) |
| | Mule | Q7Z6Z7 (Apr. 14, 2009) |
| Activator BH3-only Bcl-2 Proteins | BID | P55957 (Mar. 3, 2009) |
| | BIM | O43521 (Apr. 14, 2009) |

Other Bcl-2 proteins, if any, can be identified by homologous search using the amino acid sequence of a known Bcl-2 protein as a query.

Figure 1:
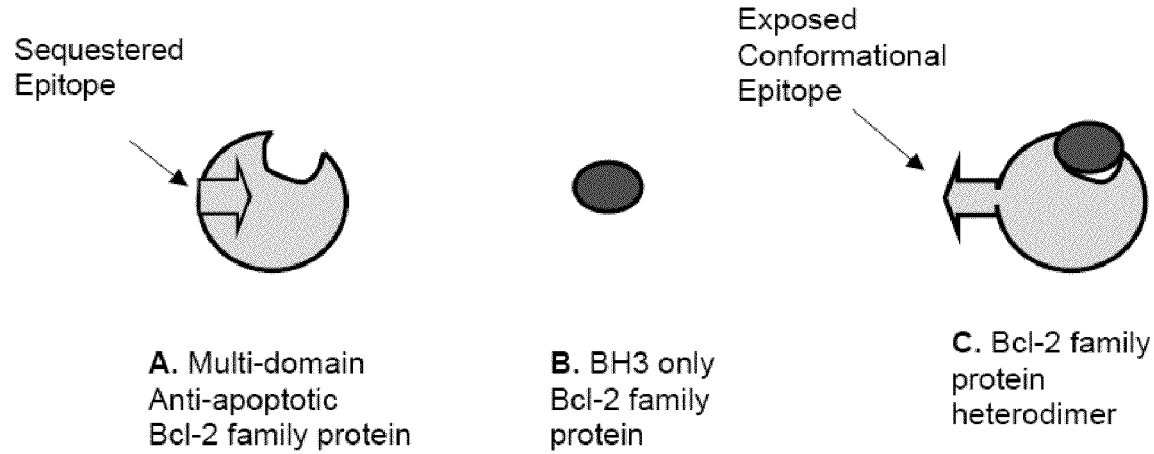
FIG. 1 is a schematic illustration depicting the conformational change of a multidomain Bcl-2 protein induced by dimerization with a BH3-only Bcl-2 protein.

It is known that members in one subgroup of Bcl-2 proteins form heterodimers with members in a different subgroup to regulate apoptosis. Formation of a heterodimer induces conformational changes in both members of the heterodimer, resulting in exposure of antigenic epitopes that are sequestered in both members before dimerization. See FIG. 1. The isolated antibody of this invention specifically recognizes such an epitope (e.g., the arrow epitope shown in FIG. 1). In other words, it only binds to a heterodimer of the Bcl-2 family, not to either non-dimerized member.

This antibody can be a whole immunoglobulin or a fragment thereof that retains antigen-binding activity. It can be a genetically modified immunoglobulin, including scFv antibody, chimeric antibody, and humanized antibody. The term "isolated antibody" used herein refers to an antibody substantially free from naturally associated molecules, i.e., the naturally associated molecules constituting at most 20% by dry weight of a preparation containing the antibody.

The antibody of this invention can be prepared by conventional methods. See, for example, Harlow and Lane, (1988) Antibodies: A Laboratory Manual, Cold Spring Harbor Laboratory, New York. In general, a heterodimer of the Bcl-2 family can be prepared by producing its two members separately by recombinant technology and then incubate both members under suitable conditions to allow formation of the heterodimer. To produce antibodies against the heterodimer, the heterodimer, optionally coupled to a carrier protein (e.g., KLH) can be mixed with an adjuvant, and injected into a host animal. Antibodies produced in the animal can then be purified by heterodimer affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage or yeast library of scFv antibodies. scFv antibodies are formed by linking the heavy and light chain fragments of the Fv region via an amino acid bridge.

Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

The antibodies prepared by any of the methods described above are confirmed for their binding to a Bcl-2 heterodimer. They are further subjected to a negative selection to exclude those that also bind to either non-dimerized member of the heterodimer. See FIG. 2. One example follows. Each of the two members, i.e., monomer A and monomer B, is labeled with a distinct fluorescent dye, i.e., dye x and dye y, respectively. Dyes x and y have different optimal emission wavelengths. The antibody is first incubated with labeled monomer A, labeled monomer B, or the A/B heterodimer (double labeled) for a suitable period and then captured by GamaBind Sepharose beads. Whether the antibody is capable of binding to either monomer or to the heterodimer can be determined based on the fluorescent signal released from the captured antibody. Antibodies that bind to the heterodimer and not to either non-dimerized member are selected. See FIG. 2.

Figure 3:
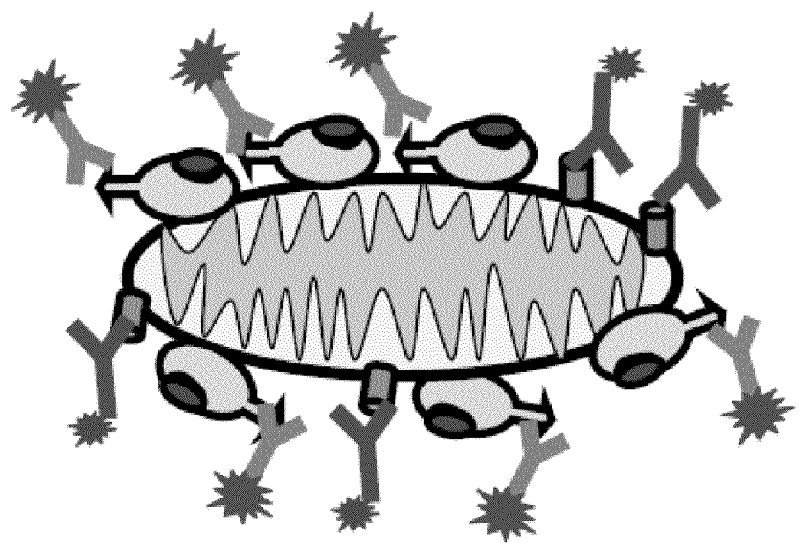
FIG. 3 is a schematic illustration depicting an immunoassay for profiling Bcl-2 heterodimers on mitochondria using the antibody of this invention, i.e., an antibody specifically recognizes Bcl-2 heterodimers, and an anti-VDAC antibody that recognizes mitochondria. Panel A: mitochondria presenting Bcl-2 heterodimers being recognized by both the antibody of this invention and an anti-VDAC antibody. Panel B: mitochondria not presenting Bcl-2 heterodimers being recognized by only the anti-VDAC antibody. Panel C: illustration of what the symbols in Panels A and B represent.
Figure 3:
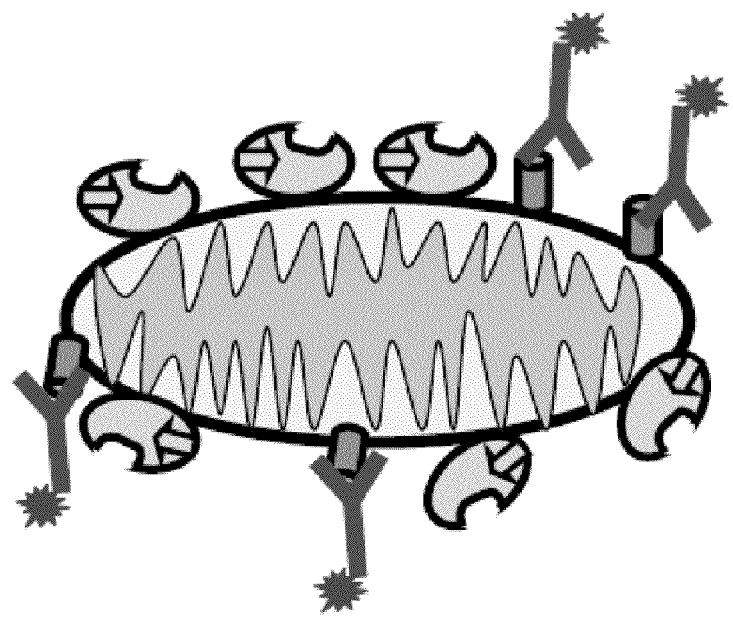
Figure 3:
Figure 3:
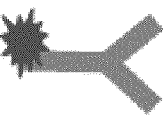
Figure 3:
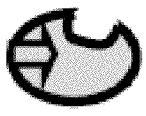
Figure 3:
Figure 3:
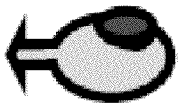
Figure 3:
Figure 3:
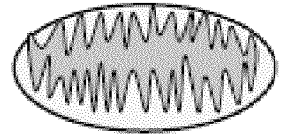

The antibody of this invention can be used to detect the presence or absence of a Bcl-2 heterodimer in a patient sample, particularly, a fixed tissue sample or a mitochondrial fraction, by conventional methods, e.g., histochemistry staining. See FIG. 3. In one example, a plurality of antibodies specific to various Bcl-2 heterodimers are used to profile the presence of particular Bcl-2 heterodimers on the outer membranes of mitochontria in multiple tissue samples from a patient. Tissues at various disease stages (e.g., malignancy stages) can be collected from the same patient. Mitochondrial fractions can be prepared from these tissues and, using a plurality of the antibodies of this invention, the fractions can be profiled for the presence/absence of Bcl-2 heterodimers.

Also disclosed herein is a method of predicting a human patient's responsiveness to a drug that interferes with formation of a particular Bcl-2 heterodimer, directly or indirectly, based on the presence of that Bcl-2 heterodimer in the patient.

It well known that Bcl-2 proteins play an essential role in regulating apoptosis via formation of heterodimers between members in different Bcl-2 sub-groups. See Table 1 above. An activator BH3-only Bcl-2 protein (i.e., BID or BIM) binds to a multi-domain pro-apoptotic Bcl-2 protein (i.e., BAX or BAK), triggering mitochondrial outer membrane permeabilization (MOMP), which leads to cell death. A multi-domain anti-apoptotic Bcl-2 protein (e.g., Bcl-2 or Mcl-1) can bind to BAX and BAK, and also sequester an activator BH3-only protein from binding to BAX or BAK. Consequently, it blocks the MOMP process, resulting in cell survival. The activity of a multi-domain anti-apoptotic Bcl-2 protein is regulated by the sensitizer BH3-only proteins. This subgroup of Bcl-2 proteins promotes apoptosis by binding to the anti-apoptotic Bcl-2 protein, displacing the activator BH3-only Bcl-2 proteins so that they are released to bind to the pro-apoptotic Bcl-2 proteins, thereby triggering the MOMP process. In short, there are two types of Bcl-2 heterodimers: (1) pro-apoptotic Bcl-2 heterodimers, formed between an activator BH3-only Bcl-2 protein and a multi-domain pro-apoptotic Bcl-2 protein or between a sensitizer BH3-only Bcl-2 protein and a multi-domain anti-apoptotic Bcl-2 protein; and (2) anti-apoptotic Bcl-2 heterodimers, formed between a multi-domain anti-apoptotic Bcl-2 protein and an activator BH3-only Bcl-2 protein or between a multi-domain anti-apoptotic Bcl-2 protein and a multi-domain pro-apoptotic Bcl-2 protein. Formation of pro-apoptotic Bcl-2 heterodimers promote apoptosis while formation of anti-apoptotic heterodimers promote cell survival.

The presence of a particular pro- or anti-apoptotic Bcl-2 heterodimer in a patient is known to indicate that patient's responsiveness to a drug that blocks formation of the particular heterodimer and inhibits its function. See, e.g., Letai, Nature Reviews Cancer, 8:121-132 (2008). In one example, the drug is a mimetic of a BH3-only protein that competes against the BH3-only protein for binding to its cognate partner. In another example, the drug targets an upstream apoptotic factor and ultimately blocks formation of a Bcl-2 heterodimer.

Many cancer drugs induce apoptosis in cancer cells by blocking formation of anti-apoptotic Bcl-2 heterodimers. The presence of a particular anti-apoptotic Bcl-2 heterodimer in a cancer patient indicates that this patient is sensitive to a drug that interferes with formation of this anti-apoptotic Bcl-2 heterodimer. See Deng, et al Cancer Cell 12(2):171-85 (2007). On the other hand, apoptosis inhibitors are used for treating neurodegenerative disease or cardiovascular disease, both of which involve apoptosis. In these cases, the presence of a particular pro-apoptotic Bcl-2 heterodimer in a neurodegenerative disease patient or a cardiovascular disease patient indicates that such a patient is sensitive to an apoptosis inhibitor that blocks formation of the particular pro-apoptotic Bcl-2 heterodimer.

Bcl-2 heterodimer profiling can also be used to predict responsiveness to drugs targeting the apoptotic pathway in patients suffering from other apoptosis-related diseases, e.g., autoimmune disease (see Adams et al., Cold Spring Harb Symp Quant Biol. 70:469-477; 2005).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Preparation of Monoclonal Antibodies Specific to Bcl-2 Heterodimers

Genes encoding human Bcl-xL, Bcl-2, and Mcl-2 are cloned and mutated to delete their transmembrane domains. The mutated genes are linked to a nucleotide sequence encoding glutathione-S-transferase (GST) and cloned into pGEX 4T-1 to obtain DNA constructs for expressing Bcl-xL(Δtd)-GST, Bcl-2(Δtd)-GST, and Mcl-2(Δtd)-GST fusion proteins. DNA constructs for expressing full length human Bax, Bak, Bak, Bim, Bid, Bad, Puma, and Noxa, all fused with GST, are prepared by recombinant technology.

All of the DNA constructs are introduced into BL21 *E. coli* cells. Positive transformants are cultured in a suitable medium and expression of the fusion proteins are induced with isopropyl-1-thio-β-D-galactopyranoside. The expressed fusion proteins are purified using Amersham Hitrap Glutathione column on the ACTA-FPLC (Amersham) and accurately quantified using spectrophotometry.

Bcl-xL(Δtd)-GST, Bcl-2(Δtd)-GST, or Mcl-2(Δtd)-GST is mixed with Bax-GST, Bak-GST, Bak-GST, Bim-GST, Bid-GST, Bad-GST, Puma-GST, or Noxa-GST at equamolar amounts in PBS. The mixture is stirred on ice for 12 hours to allow formation of heterodimers.

The heterodimmers are purified using a sepharose 12 column (Pharmacia) on a ACTA-FPLC (Amersham), following the method described in Zue et al., Protein Science 6: 781-788 (2007).

Each of the heterodimers (1 μg) is suspended in monophosphoryl lipid A plus trehalose dicorynomycolate adjuvant (Ribi Immunochem. Research Inc., Hamilton, Mont.). The mixture thus formed are injected into Balb/c mice at each hind foot pad once every 3-4 days for 14 times. Three days after the final injection, spleen cells are removed from the mice and a single cell suspension is prepared in a DMEM medium (Gibco/BRL Corp.) supplemented with 1% penicillin-streptomycin. The spleen cells are fused with murine myeloma cells P3X63AgU.1 (ATCC CRL 1597) using 35% polyethylene glycol and cultured in 96-well culture plates.

Hybridomas are selected in super DMEM [DMEM supplemented with 10% fetal calf serum FCS, 100 mM pyruvate, 100 U/ml insulin, 100 mM oxaloacetic acid, 2 mM glutamine, 1% nonessential amino acids (GIBCO/BRL), 100 U/ml penicillin, and 100 μg/ml streptomycin] containing 100 μM hypoxanthine, 0.4 μM aminopterin, and 16 μM thymidine (HAT), (Sigma Chemical Co., St. Louis, Mo.).

Hybridoma cells are fed with 200 μl of super DMEM containing 10% FCS and antibiotics. Ten days after the fusion, supernatants of the hybridoma cultures are collected and screened for the presence of antibodies that bind to the cognate heterodimer protein and/or to either member of the heterodimer (as negative controls) in a capture ELISA as described in Certo et al., Cancer Cell., 9(5):351-365 (2006).

Briefly, 96-well microtiter plates (Maxisorb; Nunc, Kamstrup, Denmark) are coated with 50 μl (1 μg/ml) of a heterodimer or a member of the heterodimer at 4° C. overnight. The plates are then washed three times with PBS containing 0.05% TWEEN 20™ (PBST) and blocked with 50 μl PBS containing 2.0% bovine serum albumin (BSA) at room temperature for 1 hour. The plates are then washed again three times with PBST. Afterwards, 100 μl of a hybridoma supernatant is added to designated wells. The plates are incubated at room temperature for 1 hour on a shaker apparatus and then washed three times with wash buffer. Next, 50 μl HRP-conjugated goat anti-mouse IgG Fc (Cappel Laboratories), diluted 1:1000 in assay buffer (0.5% bovine serum albumin, 0.05% % TWEEN 20™, 0.01% Thimersol in PBS), is added to each well. The plates are then incubated for 1 hour at room temperature on a shaker apparatus and washed three times with wash buffer, followed by addition of 50 μl of substrate DACO and incubation at room temperature for 10 minutes. 50 μl diethyl glycol were added to each well to stop the reaction and absorbance at 450 nm in each well is read in a microtiter plate reader.

Hybridoma cells producing antibodies that bind to a heterodimer but not to either member of the heterodimer are selected. These positive hybridoma cells are cloned twice and the specificity of the antibodies produced thereby are retested. The isotypes of the antibodies having the desired specificity are determined by conventional methods, e.g., using isotype specific goat anti-mouse Igs (Fisher Biotech, Pittsburgh, Pa.).

Example 2

Preparation of Polyclonal Antibodies Specific to Bcl-2 Heterodimers

New Zealand rabbits were immunized on the back and proximal limbs of the rabbits with 0.1 ml of a Bcl-2 heterodimer (50 ug/ml) prepared following the method described in Example 1. The heterodimer is pre-mixed with 50% Freund's complete adjuvant. The immunization is repeated 28th days later. On day 35, 0.5 ml of blood is obtained from each of the immunized rabbits and antibody titers in the blood samples are determined by ELISA. Antisera are collected from the arterial carotid of rabbits having high antibody titers.

The specificity of the antibodies in each antiserum is examined by conventional methods, e.g., the immunoprecipitation and FACS assays described in Examples 4 and 5 below.

Example 3

Figure 4:
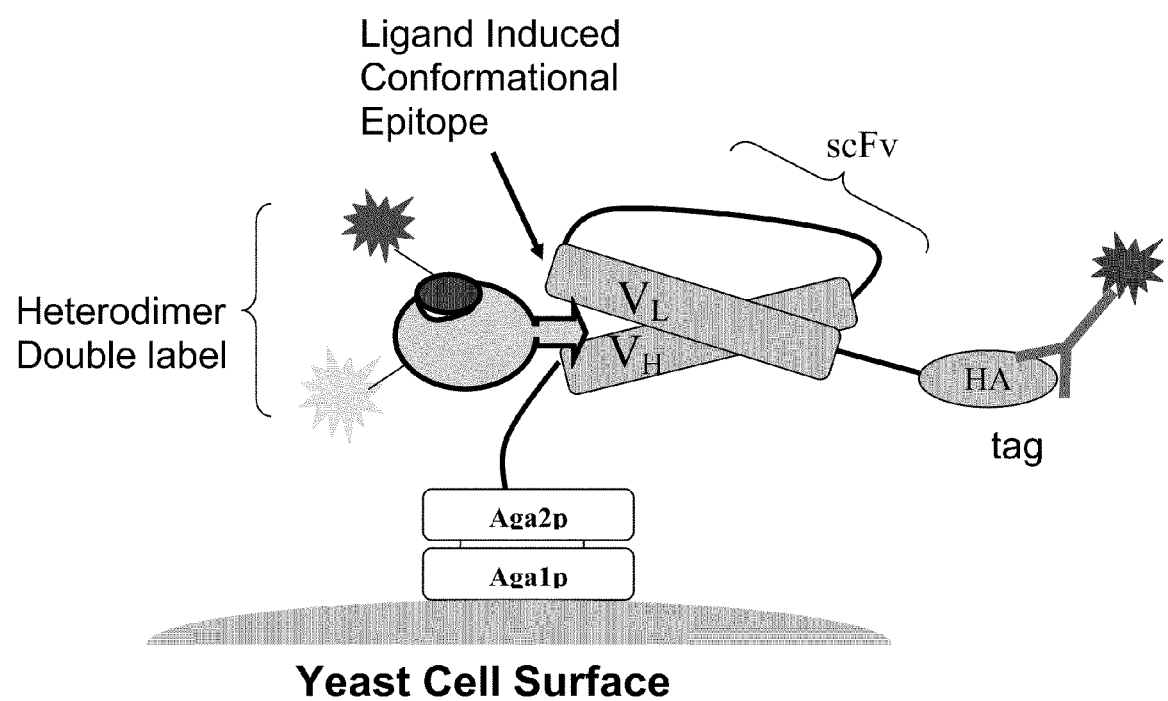
FIG. 4 is a schematic illustration showing identification of scFv antibodies specific to Bcl-2 heterodimers from a yeast display scFv library.

Screening for scFv Antibodies Specific to Bcl-2 Heterodimers Using A Yeast scFv Library A nonimmune human scFv yeast library (using expression vector pYD1) is obtained from Pacific Northwest National Laboratories. In this library, a scFv antibody, in which the heavy and light chains is connected by a flexible polypeptide linker, is fused to the adhesion subunit of the yeast agglutinin protein Aga2p and the HA-tag. Upon expression, the scFv is located on the surface of a yeast host cell via binding of Aga2P to Aga1P, a cell surface protein. See FIG. 4. Each yeast cell typically displays $1 \times 10^5$ to $1 \times 10^6$ copies of the scFv and the surface expression of the scFv. Variations in surface expression can be measured through immunofluorescence labeling of the HA-tag flanking the scFv region. See FIG. 4.

The scFv library described above is introduced into yeast strain EBY100 (Invitrogen) and scFv antibodies having the desired specificity are identified as follows. The EBY yeast cells are first grown overnight in 1 liter of SDCAA medium (containing 20 g dextrose, 6.7 g Difco yeast nitrogen base, 5 g Bacto casamino acids, 5.4 g $Na_2HPO_4$ and 8.56 g $NaH_2PO_4.H_2O$). $1 \times 10^{10}$ yeast cells from the overnight culture are precipitated by centrifugation at 2,500 g for 5 minutes and resuspended in SGCAA medium (a medium identical to SDACC except that it contains galactose instead of dextrose) to an absorbance of about 0.5-1 at 600 nm. The yeast cells are then cultured at 20° C. for 36 h to allow expression of scFv antibodies. Afterwards, the cells are collected by centrifugation at 2,500 g for 5 min. The cell pellet is washed with 25 ml PBS.

Yeast cells expressing scFv antibodies are sorted by flow cytometry. Briefly, about $1 \times 10^6$ to $1 \times 10^7$ yeast cells prepared as described above are collected via centrifugation at 14,000 g for 30 seconds, washed with 1 ml PBS buffer, and mixed with 2 μl of 10 μg/ml anti-HA phycoerythrin monoclonal antibody (SIGMA-ALDRICH) and Bcl-2/Bid heterodimer, in which Bcl-2 is labeled with FITC and Bid is labeled with Texas red. After being incubated at room temperature for 1 hour, the mixture is centrifuged at 12,000 g for 30 seconds to precipitate yeast cells. The cell pellet thus formed is resuspended in 500 μl 10 mM Tris (final cell density ~$10^6$/ml) and subjected to cell sorting by flow cytometry as follows.

A flow cytometry protocol is pre-determined using EBY100 yeast cells mixed with the anti-HA phycoerythrin antibody as a positive control and EBY100 yeast cells mixed with the double-labeled heterodimer as a negative control. Compensation is performed to reject crosstalk between the FITC, Texas red, and phycoerythrin channels of the fluorescence detector. The labeled yeast cells are loaded into a FACSAria Cell-Sorter (Becton Dickinson, Mountain View, Calif.) and gated on forward- and side scatter channels. An appropriate sort gate in the FITC/Texas red/phycoerythrin positive quadrant is drawn and the top 5% triple positive yeast cells are collected in 1 ml SDCAA media. If necessary, the top 0.1% triple-positive yeast cells are collected to ensure that only cells having high affinity to Bcl-2/Bid heterodimer is sorted.

The triple-positive cells thus identified are suspended in 10 ml SDCAA and grown over night at 30° C. These cells are then subjected to two rounds of negative selection to exclude cells expressing scFv antibodies that also bind to Bcl-2 or Bid mononer. More specifically, the cells are incubated with FITC-labeled Bcl-2 and Texas red-labeled Bid and following the same procedure described above, FITC and Texas red double negative cells are sorted. The cells thus collected are labeled with the double-labeled Bc-2/Bid heterodimer to confirm their binding to the heterodimer.

The yeast cell thus identified are diluted and plated to allow formation of individual clones. Plasmid DNAs are isolated from these clones using a Zymoprep kit (Zymo Research, Orange, Calif.) as described in Weaver-Feldhaus et al., Protien Engineering, Design & Selection vol. 18, no. 11, pp 527-536 (2005). The scFv sequence included in each plasmid DNA is determined following the method described in Chao et al., Nature Protocols 1:755-768 (2006).

The scFv antibodies thus identified are analyzed by ELISA and FACS to confirm their specificity to Bcl-2/Bid heterodimer. They can subject to mutagenesis to select for scFv antibodies having higher affinity and specificity to Bcl-2/Bid heterodimer.

Example 4

Select Antibodies Specific to Bcl-2 Heterodimers by Immunoprecipitation

Figure 2:
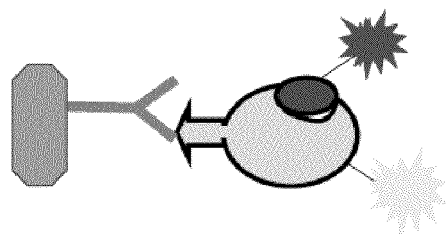
FIG. 2 is a schematic illustration depicting the process of selecting antibodies specific to Bcl-2 heterodimers via an immunoassay. Panel A: antibodies binding to a Bcl-2 heterodimer being positively selected. Panel B: antibodies binding to non-dimerized members of the heterodimer being negatively selected. Panel C: illustration of what the symbols in Panels A and B represent.
Figure 2:
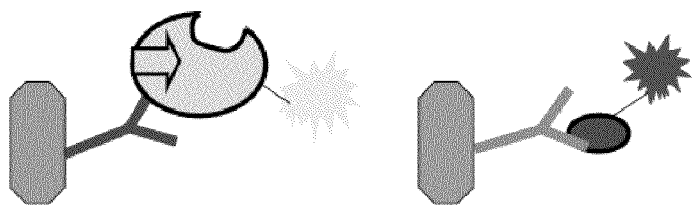
Figure 2:
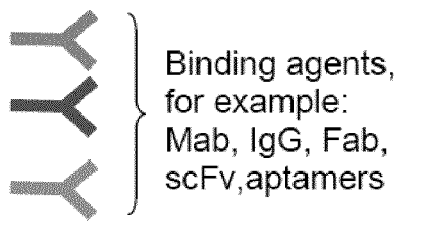
Figure 2:
Figure 2:
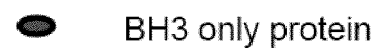
Figure 2:
Figure 2:
Figure 2:

An immunoprecipitation assay, as illustrated in FIG. 2, is performed to ensure that the antibodies obtained in Example 1 above are specific to Bcl-2 heterodimers. The two members of a Bcl-2 heterodimer are conjugated with two fluorescent probes that have distinct emission spectra, i.e., one labeled with fluorescein isothiocyanate (FITC; which emits at 488 nm) and the other labeled with Texas red (which emits at 590 nm). See Figure XX. The labeled members are incubated together to allow formation of the Bcl-2 heterodimer, following the method described in Example 1 above. 0.1 µg of the heterodimer thus formed is incubated with 50 uL of supernatant from a hydridoma clone that produces an antibody of interest in 0.5 mL PBS containing 0.05% tween-20. The non-dimerzied labeled members of the heterodimer are used as negative controls. The mixtures are incubated for 1 hour on ice to allow formation of antibody-antigen complexes and 10 ul of GammaBing-G sepharose beads (GE Healthcare, Piscataway, N.Y.) are added to the mixture. After being incubated on ice for 30 minutes on ice with rotation, the mixtures are centrifuged at 10,000 g for 30 seconds. The pellet beads, to which the antibody-antigen complexes are attached, are washed several times and measured for optical density at 488 nm ($OD_{488}$) and 590 nm ($OD_{590}$). The specificity of the antibody is determined based on the values of $OD_{488}$ and 590 nm $OD_{590}$.

Example 5

Select Antibodies Specific to Bcl-2/Bim Heterodimer by Flow Cytometry

Mitochondria from cells having a high level of Bcl2/Bim heterodimer and from cells having Bcl-2 knocked-out are purified and labeled as described in Methods Enzymol. 2000; 322:235-42 and Cancer Cell 2004; Cell 2, 183-192. See FIG. 3, Panels A and B. Briefly, the just-mentioned two types of cells are suspended in cold hypotonic lysis buffer, 259 mM sucrose, 10 mM Tris-Hcl pH (7.4), 1 mM EGTA, and homogenized in a dounce rotary Teflon pestle, followed by 6-10 expulsions through a 27-gauge needle. The fractions containing mitochondria are collected by differential centrifugation and resuspended in an assay binding buffer (125 mM KCL, 10 mM Tris-HCl (pH 7.4), 0.1 mM EGTA, pH 7.2, 20 uM ATP) to a final protein concentration of 5 mg/ml.

Twenty-five microliters of the suspension (4 mg of mitochondrial protein/ml) are suspended with PBS containing 1% FCS, (FACS buffer) and mixed with 100 µl of a hybridoma culture supernatant containing a test antibody or a test antibody in purified form (purified on Protein-G sepharose column; 10 µg/ml in the FACS buffer) in a U-bottom microtiter wells. Rhodamine-labeled polyclonal anti-VDAC-1 antibody (Merridian Life Sciences, Inc. Cincinnati Ohio), an antibody specific to mitochondria, is also added to each well. 100 µl of fluorescein isothiocyanate (FITC)-conjugated goat anti-mouse immunoglobulin are then added to the mitochondria-antibody mixture. After being incubated at 4° C. for 30 min, the mixture is washed with the FACS buffer and centrifuged at 12 g for 5 minutes to precipitate mitochondria. The mitochondrial pellet is resuspended in 150 µl of FACS buffer and analyzed by FACScan (Becton Dickinson, Mountain View, Calif.), with flow cytometry parameters pre-determined using control mitochondrial samples, i.e., unlabeled mitochondria as a negative control sample and anti-VDAC-1-Rhodamine labeled mitochondria as a positive control. The mitochondrial suspension is loaded into the flow cytometery apparatus using a FACS tube and signals released from FITC and Rhodamine are detected. If the mitochondrial suspension is double positive for both FITC and Rhodamine, it indicates that the test antibody is capable of binding to the Bcl-2/Bim heterodimer. See FIG. 3, Panel A.

Example 6

Detecting Bcl-2 Heterodimers in Fixed Cells

Cells characterized for having a prevalent Mcl-1/Bim or Bcl-2/Bid heterodimer are used in this study. See Certo et al., Cancer Cell. 9(5):351-365 (2006), Moore et al., J. Clin. Invest. 117(1):112-121 (2007), Deng et al., Cancer Cell. 12(2):171-185 (2007), and Letai, Nature Reviews Cancer 8:121 (2008). These cells, placed on cover slips, are fixed with 2-4% formaldehyde (Formaldehyde, 16%, methanol free, Polysciences, Inc.) in PBS for 15 minutes at room temperature. The cell-containing cover slips are rinsed with PBS three times, 5 minutes for each. The slips are then soaked in a blocking buffer (TBST/5% normal goat serum: to 5 ml 1×TBST add 250 µl normal goat serum) for 60 minutes. After the blocking buffer is aspirated, an antibody specific to either Mcl-1/Bim or Bcl-2/Bid heterodimer (0.1 to 15 mg/ml) is added to the slips. An anti human-VDAC-1 antibody is also added to localize mitochondria. After being incubated at 4° C. overnight, the slips are rinsed three times with PBS, 5 minutes each time. A fluorochrome-conjugated secondary antibody, diluted in a dilution buffer, is then added. After being incubated for 1-2 hours at room temperature in dark, the slips are rinsed with PBS three time, 2 minutes each time, and subsequently treated with Prolong Gold Antifade Reagent (Invitrogen, San Diego, Calif.). The slips are then sealed by painting around edges of the slips with nail polish and observed under an inverted fluorescent microscope. Localization of the antibody on mitochondria indicates that the antibody recognizes Mcl-1/Bim heterodimer or Bcl-2/Bid heterodimer.

Example 7

Detecting Bcl-2 Heterodimers in Fixed Tissue Samples

Paraffin embedded and frozen thin section tissue samples from cancer patients and healthy subjects are purchased from Imgenex, San Diego, Calif. These samples are spotted on microarray chips (4 mm×4 mm spots that are 4 mm thick). The adjacent normal tissues from the same patients/healthy subjects are also spotted on the array chips.

The microarray chips mentioned above are washed in turn with xylene three times, 5 minutes each time, 100% ethanol twice, 10 minutes each time, 95% ethanol, twice, 10 minutes each time, and finally $dH_2O$ twice, 5 minutes each time. The chips are then soaked in 1 mM EDTA, pH 8.0, heated to boiling, and then kept at a sub-boiling temperature for 15 minutes.

If the tissue samples on the microarray chips are fixed with formalin, the chips are washed in turn with 100%, 95%, 80% ethanol 3 times each, 3 minutes each time, followed by two washes with $dH_2O$, 3 minutes each. The chips are then soaked in 0.01M sodium citrate. pH 6.0 for 20 minutes.

The chips are then washed with $dH_2O$ three times, 5 minutes each time, incubated in 3% hydrogen peroxide for 10 minutes (this step is not needed for formalin fixed samples), and washed again with $dH_2O$ twice, 5 minutes each time.

Next, the chips are subjected to immunostaining using the antibodies prepared in Example 1 or an anti-VDAC1 antibody as a control. The chips are soaked in a wash buffer for 5 minutes and then in 100-400 µl of a blocking buffer (TBST containing 5% normal goat serum) for one hour. After decanting the blocking solution, the chips are incubated with 100-400 µl of an anti-Bcl-2-heterodimer antibody (primary antibody), diluted to 0.1 to 15 ug/ml for each chip, overnight at 4° C. Afterwards, the chips are washed with the wash buffer three times, 5 minutes each time, and then incubated with 100-400 µl of a biotinylated goat anti-mouse Ig antibody (the secondary antibody), which is diluted in TBST following the manufacturer's protocol, for 30 minutes at room temperature. The chips are then washed with the wash buffer three times, 5 minutes each time, and incubated with 100-400 µl ABC reagent (Vectastain ABC Kit, Vector Laboratories, Inc., Burlingame, Calif.), which is prepared following the manufacturer's instructions, for 30 minutes at room temperature. After being washed for three times with the wash buffer, the chips are incubated with 100-400 µl DAB for signal development. The chips are immersed in $dH_2O$ immediately after a color has developed thereon. When necessary, the chips are counterstained with hematoxylin and DAPI following manufacturer's instructions.

The stained chips are dehydrated by incubation sequentially in 95% ethanol two times, 10 seconds each, in 100% ethanol two times, 10 seconds each, and finally in xylene two times, 10 seconds each. The chips are then mounted with cover slips and examined using Fluorescence and UV microscopy for staining patterns. The staining patterns obtained from cancer tissue samples are compared with those obtained from adjacent normal tissues.

Example 8

Profiling Bcl-2 Heterodimers on Mitochondria Using Color Coded Micro-Beads

Figure 5:
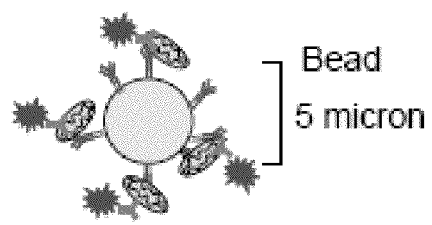
FIG. 5 is a schematic illustration depicting a Luminex bead assay for profiling Bcl-2 heterodimers in a patient sample. Panel A: multi-color beads used in the Luminex bead assay. Panel B: illustration of what the symbols in Panels A and B represent.
Figure 5:
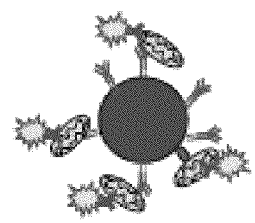
Figure 5:
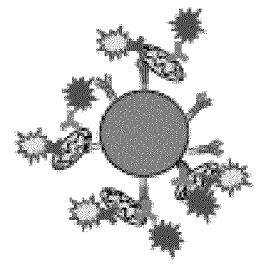
Figure 5:
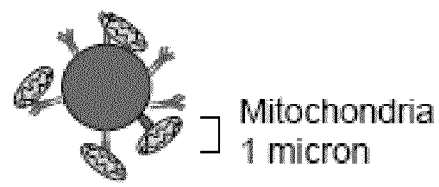
Figure 5:
Figure 5:
Figure 5:
Figure 5:
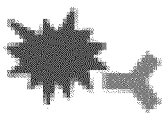

As shown in FIG. 5, micro-beads of 5 micron diameter and color coded (Luminex Incorporated) are derivatized with an anti-human VDAC-1 antibody, which recognizes mitochondria. Mitochondrial samples prepared by different patients, as described above, are incubated with different colored VDAC derivatized Luminex beads and flurescent probe-labeled antibodies specific to Bcl-2 heterodimers, as prepared by the method described in Example 1. The labeling pattern (i.e., color combination) of each mitochondrial sample is examined by conventional methods and the Bcl-2 heterodimer profile of each patient is determined based on the labeling patter. This profile can be used to diagnose certain disease indications and chemsensitivities, as well as predict outcomes of treatment for cancer or other diseases associated with apoptosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated antibody that specifically binds to a heterodimer of Bim and Mcl-1.

2. An isolated antibody that specifically binds to a heterodimer of Bim and Bcl-2.

3. An isolated antibody that specifically binds to a heterodimer of Bid and Bcl-2.

* * * * *